United States Patent [19]

Thiem et al.

[11] 3,933,868

[45] Jan. 20, 1976

[54] PROCESS FOR THE PREPARATION OF 1,5- AND 1,8-DIAMINO-ANTHRAQUINONE

[75] Inventors: Karl-Werner Thiem, Cologne; Wolfgang Auge, Odenthal; Rutger Neeff, Leverkusen; Heinz Scheiter, Leverkusen-Steinbuechel, all of Germany

[73] Assignee: Bayer Aktiengesellschaft, Leverkusen-Bayerwerk, Germany

[22] Filed: Mar. 22, 1974

[21] Appl. No.: 453,810

[30] Foreign Application Priority Data
June 14, 1973 Germany............................ 2330230

[52] U.S. Cl. ............................................... 260/382
[51] Int. Cl.$^2$.......................................... C07C 97/24
[58] Field of Search ....... 260/382, 378, 580, 583 N, 260/689

[56] References Cited
FOREIGN PATENTS OR APPLICATIONS
2,211,411   9/1972   Germany ............................ 260/382

Primary Examiner—Richard L. Raymond
Attorney, Agent, or Firm—Plumley & Tyner

[57] ABSTRACT

Process for the preparation of 1,5- and/or 1,8-diaminoanthraquinone by reaction of 1,5- and/or 1,8-dinitroanthraquinone with ammonia in organic solvents, characterised in that the reaction is carried out in ethers, aliphatic or cycloaliphatic hydrocarbons or optionally alkyl-substituted aromatic hydrocarbons or in mixtures of these compounds.

4 Claims, No Drawings

PROCESS FOR THE PREPARATION OF 1,5- AND 1,8-DIAMINO-ANTHRAQUINONE

The subject of the main patent (German Patent Application P23 14 218.9) is a process for the preparation of 1-aminoanthraquinone by reaction of 1-nitroanthraquinone with ammonia in ethers, aliphatic or cycloaliphatic hydrocarbons or optionally alkyl-substituted aromatic hydrocarbons.

It has now been found that the process of the main patent is also applicable to the reaction with dinitroanthraquinones.

German Offenlegungsschrift (German Published Specification) 2,211,411, describes a process for the preparation of aminoanthraquinones according to which aminoanthraquinones are obtained from nitroanthraquinones by reaction with ammonia, ammonium salts or amides in the presence of an amide which is liquid under the reaction conditions. The reaction is carried out at elevated temperature, preferably at between 100° and 180°C, and optionally under pressure. The amides used are low molecular organic amides, for example formamide, urea or N-methylpyrrolidone.

The reaction mixture is worked up according to methods which are in themselves known, for example by distilling off the amide or by precipitating the aminoanthraquinone with water, or by extraction.

The said Offenlegungsschrift (Published Specification) mentions that the process is also suitable for the preparation of $\alpha,\alpha$-diaminoanthraquinones from $\alpha,\alpha$-dinitroanthraquinones. If this process is followed, the $\alpha,\alpha$-diaminoanthraquinones are produced in low yields only.

The $\alpha,\alpha$-diaminoanthraquinone thus obtained is insufficiently pure for further conversion to dyestuffs.

It has now been found that purer $\alpha,\alpha$-diaminoanthraquinones are obtained, in higher yields, if $\alpha,\alpha$-dinitroanthraquinones, in ethers, aliphatic and cycloaliphatic hydrocarbons, optionally alkyl-substituted aromatic hydrocarbons or mixtures of these solvents, are reacted with ammonia, preferably under pressure and at elevated temperature.

Examples of suitable $\alpha,\alpha$-dinitroanthraquinones are 1,5- and 1,8-dinitroanthraquinone.

Suitable ethers are, in particular, aliphatic, cycloaliphatic and aromatic ethers, such as dibenzyl ether, di-sec.-butyl ether, diisopentyl ether, ethylene glycol dimethyl ether, diethylene glycol dimethyl ether, diethylene glycol diethyl ether, methoxycyclohexane, ethoxycyclohexane, dicyclohexyl ether, anisole, phenetole, diphenyl ether, 2-methoxynaphthalene, tetrahydrofurane, dioxane, amyl phenyl ether, benzyl isoamyl ether, dibenzyl ether, diglycol di-n-butyl-ether, glycol methylene ether and methyl benzyl ether.

Examples of suitable aliphatic and cycloaliphatic hydrocarbons are n-pentane, n-hexane, n-heptane, cyclohexane, methylcyclohexane, cyclododecane, decalin, cycloheptane, cyclopentane, n-decane, 1,2-dimethylcyclohexane, 1,3-dimethylcyclohexane, 1,4-dimethylcyclohexane, 2,2-dimethylpentane, 2,3-dimethylpentane, 2,4-dimethylpentane, 3,3-dimethylpentane, isopropylhexane, methylcyclohexane, 2-methylheptane, 3-methylheptane, 4-methylheptane, 2-methylhexane, 3-methylhexane, 2-methyloctane, 3-methyloctane, 4-methyloctane, 2-methylpentane, 3-methylpentane, n-octane, pentaisobutane, triethylamine, 2,2,3-trimethylpentane, 2,2,4-trimethylpentane and 2,3,3-trimethylpentane.

Examples of suitable aromatic hydrocarbons are toluene, o-, m- and p-xylene, isopropylbenzene, trimethylbenzene, benzene, diethylbenzene, tetramethylbenzene, di-isopropylbenzene, isododecylbenzene, tetralin, naphthalene, methylnaphthalene, di-phenyl, diphenylmethane, o-, m- and p-cymene, dibenzyl, dihydronaphthalene, 2,2'-dimethyldiphenyl, 2,3'-dimethyldiphenyl, 2,4'-dimethyldiphenyl, 3,3'-dimethyldiphenyl, 1,2-dimethylnaphthalene, 1,4-dimethylnaphthalene, 1,6-dimethylnaphthalene, 1,7-dimethylnaphthalene, 1,1-diphenylethane, hexamethylbenzene, isoamylbenzene, pentamethylbenzene, 1,2,3,4-tetramethylbenzene, 1,2,3,5-tetramethylbenzene, 1,2,7-trimethylnaphthalene and 1,2,5-trimethylnaphthalene.

The process according to the invention is carried out under the conditions of the process according to the main patent, in particular with regard to the solvents, the temperature, the further working up and the molar ratio; here and in the following text, the molar ratio is to be understood as the molar ratio of ammonia to moles of $\alpha,\alpha$-dinitroanthraquinone.

The reaction time depends on the temperature, the pressure and the molar ratio and in particular the reaction velocity increases with increasing temperature, increasing pressure and increasing molar ratio. Thus, for example, at a molar ratio of 60:1 (40:1 or 30:1) at 150° and pressures above 60 atmospheres the reaction is complete after 4 (7 or 11) hours respectively, whilst, for example, at 200° (100°), a molar ratio of 20:1 (80:1) at pressures above 70 atmospheres 1 (15) hours are required for complete reaction.

The process can be carried out continuously or discontinuously.

The reaction mixture can be worked up according to customary methods, for example by filtering off the product which has crystallised out from the organic solvent after cooling to room temperature. The mother liquor obtained at the same time can be recycled to the process.

The reaction mixture can, however, also be worked up by distilling off the solvent or precipitating the diaminoanthraquinones with the aid of a diluent which lowers the solubility of the $\alpha,\alpha$-diaminoanthraquinones in the reaction solution (for example petroleum ether).

Since the solubility of 1,5-diaminoanthraquinone in organic solvents is substantially less than that of 1,8-diaminoanthraquinone, the working up of the reaction mixture can also be combined with a fractional precipitation in which 1,5-diaminoanthraquinone is first precipitated, and on further addition of the diluent 1,8-diaminoanthraquinone is precipitated.

The mother liquor obtained, or the distilled solvent, can be recycled to the process. The water produced in the reaction can be eliminated from the system.

If necessary, the reaction product can be purified further by treatment with acids, for example sulphuric acid, or by distillation in vacuo.

Accordingly, the subject of the present invention is a process for the preparation of $\alpha,\alpha$-diaminoanthraquinones, which is characterised in that $\alpha,\alpha$-dinitroanthraquinones, in ethers, aliphatic or cycloaliphatic hydrocarbons or optionally alkyl-substituted aromatic hydrocarbons or mixtures of these compounds, are reacted with ammonia, preferably under pressure, in particular at not less than 20 and preferably at not less than 50 atmospheres, and at molar ratios of ammonia to α,α-dinitroanthraquinones of at least 4:1, especially 10:1 to 80:1 and preferably 20:1 to 40:1, at an elevated temperature, preferably at 100°–220°C and especially at 140°–200°C.

The process according to the invention can also be used for the reaction of nitroanthraquinone mixtures which inter alia contain 1-nitroanthraquinone and 1,5- and/or 1,8-dinitroanthraquinone. In that case, products which contain 1-aminoanthraquinone and 1,5- and/or 1,8-diaminoanthraquinone are obtained. Pure 1-aminoanthraquinone can be conveniently isolated from such products by distillation in vacuo.

As compared to the process known from German Offenlegungsschrift (German Published Specification) 2,211,411, the process according to the invention has the advantage that the organic solvents according to the invention do not participate in the reaction and the desired α,α-diaminoanthraquinones are obtained in substantially better yields.

EXAMPLE 1

A mixture of 298 g of a dinitroanthraquinone mixture (41.7% of 1,5-dinitroanthraquinone and 40.6% by weight of 1,8-dinitroanthraquinone) and 3 liters of toluene is reacted in an autoclave with 340 g of liquid ammonia for 12 hours at 150° and a pressure of 60 atmospheres (molar ratio 20:1).

After releasing the pressure, and cooling to room temperature, the reaction mixture is filtered and the residue is washed with a little solvent and dried in vacuo.

Yield: 230 g (40.5% by weight of 1,5-diaminoanthraquinone, 94% of theory; 37.8% by weight of 1,8-diaminoanthraquinone, 90% of theory).

The unreacted ammonia and the filtrate can be recycled to the process.

EXAMPLE 2

298 g of 1,5-dinitroanthraquinone (90% by weight; 10% by weight of 1,8-dinitroanthraquinone) in 2 liters of toluene are reacted with 680 g of liquid ammonia (molar ratio 40:1) in an autoclave at 150° and 50 atmospheres for 7 hours. The reaction mixture is worked up as described in Example 1. Yield: 219 g (90% by weight of 1,5-diaminoanthraquinone, 92% of theory).

Similar yields and purities result if instead of toluene, benzene, 1,3,5-trimethylbenzene, isopropylbenzene, isododecylbenzene, diphenylmethane, n-hexane, n-heptane, decalin, tetralin, methylcyclohexane, cyclododecane, n-dipropyl ether, dibutyl ether, diethylene glycol dimethyl ether, diethylene glycol diethyl ether, methoxycyclohexane, dicyclohexyl ether, anisole, phenetole, diphenyl ether, tetrahydrofurane, dioxane, o-xylene, m-xylene, p-xylene or mixtures of these solvents are used.

EXAMPLE 3

298 g of 1,8-dinitroanthraquinone (90% by weight of 1,8-dinitroanthraquinone) in 1 liter of xylene are reacted with 1.02 kg of liquid ammonia (molar ratio 60:1) in an autoclave at 110 atmospheres and 150° for 4 hours and the mixture is worked up as described. Yield: 190 g (90% by weight of 1,8-diaminoanthraquinone, 80% of theory). Similar yields and purities result if instead of xylene the solvents mentioned in Example 2 are used.

EXAMPLE 4

298 g of a mixture (53.9% by weight of 1,5-dinitroanthraquinone; 46.1% by weight of 1,8-dinitroanthraquinone) in 1 liter of cyclohexane are reacted with 102 g of liquid ammonia (molar ratio 6:1) at 200° in an autoclave at 110 atmospheres for 6 hours. After working up as described in Example 1, 230 g (51.1% by weight of 1,5-diaminoanthraquinone, 92% of theory; 40.9% by weight of 1,8-diaminoanthraquinone, 86% of theory) are obtained.

EXAMPLE 5

298 g of the dinitroanthraquinone mixture indicated in Example 4, in 2 liters of glycol dimethyl ether, are reacted with 1.36 kg of liquid ammonia (molar ratio 80:1) at 100° in an autoclave at a pressure of 60 atmospheres for 15 hours.

The reaction mixture is introduced into water. The precipitate which separates out is filtered off, washed with water and dried.

Yield: 230 g (53% by weight of 1,5-diaminoanthraquinone, 95% of theory; 40.1% by weight of 1,8-diaminoanthraquinone; 85% of theory).

EXAMPLE 6

298 g of dinitroanthraquinone mixture indicated in Example 4, in 2 liters of xylene, are reacted with 510 g of ammonia (molar ratio 30:1) for 11 hours at 150° in an autoclave at 50 atmospheres. After working up as described in Example 1, 232 g (52.0% by weight of 1,5-diaminoanthraquinone, 94% of theory; 42.3% by weight of 1,8-diaminoanthraquinone, 89% of theory) are obtained.

EXAMPLE 7

According to DOS (German Published Specification) 2,211,411 (analogous to Example 1).

29.8 g of a mixture (47.6% by weight of 1,5-dinitroanthraquinone; 38.5% by weight of 1,8-dinitroanthraquinone) are suspended in 111 g of formamide. Ammonia gas is passed in at 155°. After 4 hours, dinitroanthraquinone is no longer detectable by thin layer chromatography. The reaction mixture is worked up by distilling off the formamide, washing the residue with water and drying it.

Yield: 24.4 g (9.7% by weight of 1,5-diaminoanthraquinone, 22% of theory; 20.2% by weight of 1,8-diaminoanthraquinone, 53% of theory).

If the reaction is carried out under otherwise identical conditions but under pressure, at a molar ratio of 20:1, approximately the same result is obtained.

We claim:

1. Process for the preparation of 1,5- and/or 1,8-diaminoanthraquinone which comprises reacting at 100°–220°C and a pressure of at least 20 atmospheres 1,5- and/or 1,8-dinitroanthraquinone with at least 4 mols of ammonia per mol of dinitroanthraquinone in an organic solvent selected from the group consisting of ethers, aliphatic hydrocarbons, cycloaliphatic hydrocarbons, aromatic hydrocarbons, alkyl-substituted aromatic hydrocarbons, and mixtures thereof.

2. Process of claim 1 wherein the solvent is an alkylbenzene.

3. Process of claim 1 wherein the reaction is carried out at a pressure of at least 50 atmospheres, and at a molar ratio of ammonia to dinitroanthraquinone of 10:1 to 80:1.

4. Process of claim 1 wherein the reaction is carried out at a temperature of 140° to 200°.

* * * * *